(12) United States Patent
Rathbun et al.

(10) Patent No.: US 7,731,721 B2
(45) Date of Patent: Jun. 8, 2010

(54) PLATING SYSTEM WITH MULTIPLE FUNCTION DRILL GUIDE

(75) Inventors: David S. Rathbun, Gap, PA (US); Lawrence J. Binder, Jr., Langhorne, PA (US); Sean S. Suh, Plymouth Meeting, PA (US); Pascal Stihl, Grenchen (CH); Christopher J. Ryan, West Chester, PA (US); Lan Anh Duong, Denver, PA (US)

(73) Assignee: Synthes USA, LLC, West Chester, PA (US)

( * ) Notice: Subject to any disclaimer, the term of this patent is extended or adjusted under 35 U.S.C. 154(b) by 497 days.

(21) Appl. No.: 10/619,472

(22) Filed: Jul. 16, 2003

(65) Prior Publication Data
US 2005/0015092 A1    Jan. 20, 2005

(51) Int. Cl.
*A61B 17/58* (2006.01)
*A61B 17/60* (2006.01)

(52) U.S. Cl. .............. 606/96; 606/86; 606/87; 606/88; 606/89; 606/97; 606/98

(58) Field of Classification Search ............. 606/96–98, 606/69, 70, 71
See application file for complete search history.

(56) References Cited

U.S. PATENT DOCUMENTS

| | | | |
|---|---|---|---|
| 1,831,813 A | 11/1931 | Levedahl | |
| 2,181,746 A | 11/1939 | Siebrandt | |
| 2,200,120 A | 5/1940 | Nauth | |
| 2,424,485 A | 7/1947 | Miller | |
| 2,494,229 A | 1/1950 | Collison | |
| 2,607,339 A | 8/1952 | Price | |
| 2,670,637 A | 2/1954 | Edmunds | |
| 2,674,906 A | 4/1954 | Timpner | |
| 3,071,030 A | 1/1963 | Larry | |
| 3,540,322 A | 11/1970 | Swanson | |
| 3,727,611 A | 4/1973 | Schultz | |
| 3,867,932 A * | 2/1975 | Huene | 606/80 |
| 4,119,092 A | 10/1978 | Gil | |
| 4,388,921 A | 6/1983 | Sutter et al. | |
| 4,450,835 A | 5/1984 | Asnis et al. | |
| 4,465,065 A * | 8/1984 | Gotfried | 606/65 |
| 4,493,317 A | 1/1985 | Klaue | |
| 4,646,413 A | 3/1987 | Nall et al. | |

(Continued)

FOREIGN PATENT DOCUMENTS

CH          655646 A5    5/1986

(Continued)

OTHER PUBLICATIONS

Supplemental European Search Report dated Jul. 16, 2008.

*Primary Examiner*—Thomas C Barrett
*Assistant Examiner*—Sameh Boles
(74) *Attorney, Agent, or Firm*—Stroock & Stroock & Lavan LLP (57) ABSTRACT

A bone fixation system including a bone plate and surgical drill guide is provided. The drill guide assembly includes one or more alignment drill tubes that are remotely aligned with corresponding fastener holes in the bone plate, and a plate holder to engage a hole in the bone plate. The surgical drill guide is releasably lockable to the plate holder.

7 Claims, 8 Drawing Sheets

U.S. PATENT DOCUMENTS

| | | | |
|---|---|---|---|
| 4,668,134 A | 5/1987 | Vindez | |
| D291,246 S | 8/1987 | Lower | |
| 4,744,353 A | 5/1988 | McFarland | |
| 4,787,377 A | 11/1988 | Laboureau | |
| 4,788,970 A | 12/1988 | Karas et al. | |
| 4,791,918 A | 12/1988 | Von Hasselbach | |
| 4,803,976 A | 2/1989 | Frigg et al. | |
| 4,872,451 A | 10/1989 | Moore et al. | |
| 4,898,502 A | 2/1990 | Becher | |
| 4,911,153 A | 3/1990 | Border | |
| 4,941,781 A | 7/1990 | Becher | |
| 4,969,781 A | 11/1990 | Fahrner et al. | |
| 5,026,376 A | 6/1991 | Greenberg | |
| 5,030,219 A | 7/1991 | Matsen, III et al. | |
| 5,054,968 A | 10/1991 | Eckman | |
| 5,071,293 A | 12/1991 | Wells | |
| 5,112,336 A | 5/1992 | Krevolin et al. | |
| 5,133,720 A | 7/1992 | Greenberg | |
| 5,147,367 A | 9/1992 | Ellis | |
| 5,154,720 A | 10/1992 | Trott et al. | |
| 5,207,753 A | 5/1993 | Badrinath | |
| 5,250,055 A | 10/1993 | Moore et al. | |
| 5,281,056 A | 1/1994 | Lawson et al. | |
| 5,306,278 A | 4/1994 | Dahl et al. | |
| 5,312,412 A | 5/1994 | Whipple | |
| 5,324,295 A | 6/1994 | Shapiro | |
| 5,342,363 A * | 8/1994 | Richelsoph | 606/79 |
| 5,364,399 A | 11/1994 | Lowery et al. | |
| D357,534 S | 4/1995 | Hayes | |
| 5,409,493 A | 4/1995 | Greenberg | |
| D359,557 S | 6/1995 | Hayes | |
| 5,423,826 A | 6/1995 | Coates et al. | |
| 5,429,641 A | 7/1995 | Gotfried | |
| 5,437,677 A | 8/1995 | Shearer et al. | |
| 5,458,602 A | 10/1995 | Goble et al. | |
| 5,484,446 A | 1/1996 | Burke et al. | |
| 5,507,801 A | 4/1996 | Gisin et al. | |
| 5,531,751 A * | 7/1996 | Schultheiss et al. | 606/96 |
| 5,575,794 A | 11/1996 | Walus et al. | |
| 5,584,839 A | 12/1996 | Gieringer | |
| 5,595,193 A | 1/1997 | Walus et al. | |
| 5,601,550 A | 2/1997 | Esser | |
| 5,601,553 A | 2/1997 | Trebing et al. | |
| 5,624,447 A | 4/1997 | Myers | |
| 5,634,927 A | 6/1997 | Houston et al. | |
| 5,637,112 A | 6/1997 | Moore et al. | |
| D382,056 S | 8/1997 | Kammerer | |
| 5,669,915 A | 9/1997 | Caspar et al. | |
| 5,676,666 A | 10/1997 | Oxland et al. | |
| 5,681,311 A | 10/1997 | Foley et al. | |
| 5,700,267 A | 12/1997 | Urbanski | |
| 5,722,978 A | 3/1998 | Jenkins, Jr. | |
| 5,725,532 A | 3/1998 | Shoemaker | |
| 5,741,266 A | 4/1998 | Moran et al. | |
| 5,743,916 A | 4/1998 | Greenberg et al. | |
| 5,746,743 A | 5/1998 | Greenberg | |
| 5,746,763 A | 5/1998 | Benderev et al. | |
| 5,749,884 A | 5/1998 | Benderev et al. | |
| 5,755,721 A * | 5/1998 | Hearn | 606/96 |
| 5,766,221 A | 6/1998 | Benderev et al. | |
| 5,769,856 A | 6/1998 | Dong et al. | |
| D397,220 S | 8/1998 | Kumar et al. | |
| D398,996 S | 9/1998 | Simmons et al. | |
| 5,836,950 A | 11/1998 | Hansson | |
| RE36,020 E | 12/1998 | Moore et al. | |
| 5,851,207 A | 12/1998 | Cesarone | |
| D404,126 S | 1/1999 | Asfora | |
| 5,873,289 A * | 2/1999 | Jarvis | 81/177.85 |
| 5,888,034 A | 3/1999 | Greenberg | |
| 5,895,390 A | 4/1999 | Moran et al. | |
| 5,910,143 A | 6/1999 | Cripe et al. | |
| 5,913,860 A | 6/1999 | Scholl | |
| 5,938,686 A | 8/1999 | Benderev et al. | |
| 5,947,654 A | 9/1999 | Blankenship et al. | |
| 5,951,561 A | 9/1999 | Pepper et al. | |
| 5,954,722 A | 9/1999 | Bono | |
| 5,957,927 A | 9/1999 | Magee et al. | |
| 5,961,257 A | 10/1999 | Bettini et al. | |
| 5,961,530 A | 10/1999 | Moore et al. | |
| 5,976,145 A * | 11/1999 | Kennefick, III | 606/80 |
| 6,007,535 A | 12/1999 | Rayhack et al. | |
| 6,013,083 A | 1/2000 | Bennett | |
| 6,019,767 A | 2/2000 | Howell | |
| 6,036,696 A | 3/2000 | Lambrecht et al. | |
| 6,059,789 A | 5/2000 | Dinger et al. | |
| 6,066,142 A | 5/2000 | Serbousek et al. | |
| 6,113,637 A | 9/2000 | Gill et al. | |
| 6,139,550 A | 10/2000 | Michelson | |
| D433,506 S | 11/2000 | Asfora | |
| 6,143,012 A | 11/2000 | Gausepohl | |
| 6,152,927 A | 11/2000 | Farris et al. | |
| 6,193,721 B1 | 2/2001 | Michelson | |
| 6,193,723 B1 | 2/2001 | Cripe et al. | |
| 6,206,881 B1 | 3/2001 | Frigg et al. | |
| 6,206,886 B1 | 3/2001 | Bennett | |
| 6,210,415 B1 | 4/2001 | Bester | |
| 6,235,034 B1 | 5/2001 | Bray | |
| 6,238,400 B1 | 5/2001 | Bays | |
| 6,241,729 B1 | 6/2001 | Estes et al. | |
| 6,258,091 B1 | 7/2001 | Sevrain et al. | |
| 6,283,969 B1 | 9/2001 | Grusin et al. | |
| 6,287,313 B1 | 9/2001 | Sasso | |
| 6,299,616 B1 | 10/2001 | Beger | |
| 6,306,136 B1 | 10/2001 | Baccelli | |
| 6,306,139 B1 | 10/2001 | Fuentes | |
| 6,322,562 B1 | 11/2001 | Wolter | |
| 6,330,845 B1 | 12/2001 | Meulink | |
| 6,342,056 B1 | 1/2002 | Mac-Thiong et al. | |
| 6,342,057 B1 | 1/2002 | Brace et al. | |
| 6,361,537 B1 | 3/2002 | Anderson | |
| 6,371,959 B1 | 4/2002 | Trice | |
| 6,379,364 B1 | 4/2002 | Brace et al. | |
| 6,383,186 B1 | 5/2002 | Michelson | |
| 6,398,783 B1 | 6/2002 | Michelson | |
| 6,416,518 B1 | 7/2002 | DeMayo | |
| 6,416,528 B1 | 7/2002 | Michelson | |
| 6,419,678 B1 | 7/2002 | Asfora | |
| 6,428,542 B1 | 8/2002 | Michelson | |
| 6,436,103 B1 | 8/2002 | Suddaby | |
| 6,447,512 B1 * | 9/2002 | Landry et al. | 606/61 |
| 6,454,771 B1 | 9/2002 | Michelson | |
| 6,475,190 B2 | 11/2002 | Young | |
| 6,491,714 B1 | 12/2002 | Bennett | |
| 6,494,913 B1 * | 12/2002 | Huebner | 623/19.11 |
| 6,524,238 B2 | 2/2003 | Velikaris et al. | |
| 6,524,312 B2 | 2/2003 | Landry et al. | |
| 6,527,776 B1 | 3/2003 | Michelson | |
| 6,533,786 B1 | 3/2003 | Needham et al. | |
| 6,558,089 B2 | 5/2003 | DeBlasio | |
| 6,562,046 B2 | 5/2003 | Sasso | |
| 6,565,571 B1 | 5/2003 | Jackowski et al. | |
| 6,960,216 B2 * | 11/2005 | Kolb et al. | 606/96 |
| 2001/0027320 A1 | 10/2001 | Sasso | |
| 2001/0047172 A1 | 11/2001 | Foley et al. | |
| 2002/0004661 A1 | 1/2002 | Sevrain et al. | |
| 2002/0022847 A1 | 2/2002 | Ray, III et al. | |
| 2002/0045896 A1 | 4/2002 | Michelson | |
| 2002/0082606 A1 | 6/2002 | Suddaby | |
| 2002/0120273 A1 | 8/2002 | Needham et al. | |
| 2002/0128655 A1 | 9/2002 | Michelson | |
| 2002/0133172 A1 | 9/2002 | Lambrecht et al. | |
| 2002/0147450 A1 | 10/2002 | LeHuec et al. | |
| 2002/0183754 A1 | 12/2002 | Michelson | |
| 2003/0018335 A1 | 1/2003 | Michelson | |

| | | | | | | |
|---|---|---|---|---|---|---|
| 2003/0032865 | A1* | 2/2003 | Estes et al. ............ 600/226 | FR | 2713473 A1 | 6/1995 |
| 2003/0040748 | A1 | 2/2003 | Aikins et al. | FR | 2735008 A1 | 12/1996 |
| 2003/0040752 | A1 | 2/2003 | Kitchens | FR | 2784570 A1 | 4/2000 |
| 2003/0040753 | A1 | 2/2003 | Daum et al. | GB | 2243316 A | 10/1991 |
| 2003/0045880 | A1 | 3/2003 | Michelson | GB | 2324967 A | 11/1998 |
| 2003/0055430 | A1 | 3/2003 | Kim | JP | 2236331 A | 9/1990 |
| 2003/0083661 | A1 | 5/2003 | Orbay et al. | JP | 5031116 A | 2/1993 |
| 2003/0083667 | A1 | 5/2003 | Ralph et al. | JP | 10-328205 A | 12/1998 |
| 2004/0186482 | A1* | 9/2004 | Kolb et al. ............ 606/96 | JP | 2001-245894 A | 9/2001 |

FOREIGN PATENT DOCUMENTS

| | | |
|---|---|---|
| DE | 3222037 A1 | 4/1984 |
| DE | 4238582 A1 | 5/1994 |
| EP | 281763 A2 | 9/1988 |
| EP | 495488 A2 | 1/1991 |
| EP | 506213 A1 | 2/1991 |
| EP | 518071 A1 | 12/1992 |
| EP | 591985 A1 | 4/1994 |
| EP | 518071 B1 | 10/1994 |
| EP | 281763 B1 | 12/1998 |
| EP | 962190 A2 | 12/1999 |
| EP | 995403 A1 | 4/2000 |
| EP | 1132052 A2 | 9/2001 |
| WO | WO 93/19678 A2 | 10/1993 |
| WO | WO 95/11632 A1 | 5/1995 |
| WO | WO 96/05778 A1 | 2/1996 |
| WO | WO 96/15727 A1 | 5/1996 |
| WO | WO 96/20650 A1 | 7/1996 |
| WO | WO 98/34553 A1 | 8/1998 |
| WO | WO 99/21502 A1 | 5/1999 |
| WO | WO 99/52453 A2 | 10/1999 |
| WO | WO 01/01874 A1 | 1/2001 |
| WO | WO 01/19267 | 3/2001 |
| WO | WO 02/02999 A1 | 1/2002 |
| WO | WO 02/080791 A1 | 10/2002 |
| WO | WO 03/007826 A1 | 1/2003 |

* cited by examiner

PLATING SYSTEM WITH MULTIPLE FUNCTION DRILL GUIDE

FIELD OF THE INVENTION

The present invention relates to a bone fixation system including a plate and surgical drill guide that are releasably attachable to each other for providing a precise alignment therebetween. More particularly, the present invention relates to a bone plate having fastener holes oriented at predetermined angles with respect to the plate and a plate holder and surgical drill guide assembly with at least one alignment drill guiding barrel that is aligned with the respective fastener holes in a bone plate for drilling the holes at the proper angle.

BACKGROUND OF THE INVENTION

The use of surgical fixation plates for a variety of orthopedic applications is widely accepted. The plates are used by surgeons to mend, align, and alter compression of patient's bones, and are typically fastened to the bones with a plurality of fasteners such as screws that are installed through holes in the plate. Proper orientation and alignment of fasteners and secure surgical fixation of the plates is advantageous in avoiding future complications after implantation.

Bone plates used in spinal applications must be installed with special care, as the plates are used for long term, intervertebral fixation, bone-fragment fixation, and anterior decompression in the cervical region of the spine. The margin for error in spinal surgery is quite small, particularly because of the sensitivity of the spinal cord and the risk inherent with invasive procedures around the spinal cord. In particular, the dimensions of vertebral bone available for setting fasteners are fairly limiting.

Each fixation fastener should properly align with its associated plate hole so that each screw is seated correctly with the plate and enters the bone at an appropriate angle. Any misalignment of the screw within the plate hole risks tissue damage. In addition, improperly seated screws may result in an unstable or insecure connection of the plate to the bony material, thus potentially defeating the usefulness of the plate. Locking plates, in particular, demand precise fastener alignment.

SUMMARY OF THE INVENTION

The invention relates to a bone plate, a surgical drill guide assembly comprising at least one alignment drill tube configured to receive and guide a surgical drill bit; and a plate holder that couples to the plate and to the drill guide assembly. The drill guide assembly is configured and dimensioned to allow it to couple with the plate holder and plate to provide a fixed dimensional and angular alignment between the alignment drill tube and the bone plate.

The bone plate has two or more pairs of fixation holes and may have one or more slots along the central longitudinal axis of the plate. The fixation holes are preferably conical and preferably threaded. The bone screws to be used with the bone plate preferably have threaded or unthreaded conical heads to match the fixation holes in the bone plate. The fixation holes in the bone plate may be angled toward the central axis of the bone plate up to about 10°, and may also be angled up to about 15° upward or downward along the direction of the longitudinal axis of the bone plate which is generally aligned in the direction of the length of the spine. The slot(s) may be threaded or have a counterbore at its ends to allow coupling of the drill guide assembly or the plate holder. The bone plate may have any thickness, and its thickness may vary along its length and width, although 2.2 mm is an exemplary thickness. The plate may also have a step feature or flange to facilitate placing the plate on the sacral promontory.

The plate holder may include a rod having a circular cross section along with a short threaded section for coupling with a threaded hole in the plate, a short non-circular section, such as, for example, a hexagonal section on the end opposite from the threaded end, and a radial groove between the ends. The plate holder attaches to the plate and allows the user to manipulate the plate from a location remote from and without touching the plate.

Preferably, the drill guide assembly includes a handle member, an offset handle stem, an outer stem, a release sleeve on the outer stem, captive ball detents in the wall of the outer stem to engage the radial groove of the plate holder rod, and a release sleeve spring that biases the release sleeve axially away from the end of the outer stem opposite the bone plate. The release sleeve is preferably captively attached to the outer stem such that it may rotate about the outer stem and has limited axial movement with respect to the outer stem. Pressing the release sleeve against the bias of the spring allows radial movement of the captive ball detents in the wall of the outer stem due to a tapered inner surface of the release sleeve or a section of the release sleeve with an increased inner diameter.

Coupling of the drill guide assembly to the plate holder is accomplished by sliding the outer stem of the drill guide assembly over the plate holder and aligning the non-circular end of the plate holder with a matching non-circular hole at the end of the outer stem of the drill guide assembly. The captive ball detents engage the radial groove of the plate holder and lock the drill guide assembly to the plate holder when the release sleeve is allowed to return to its spring-biased position. The release sleeve may have a non-circular hole the perimeter of which engages the perimeter of the matching non-circular end of the plate holder. The release sleeve can be rotated in relation to the outer stem to allow screwing and unscrewing of the plate holder from the bone plate while the remainder of the drill guide assembly remains stationary. Although the connection between the drill guide assembly and the plate holder has been described as a stem coaxial with and sliding over a rod, other embodiments are possible including, for example, a drill guide assembly with a stem attaching to the side of a plate holder.

The drill guide assembly may include either one or two guiding barrels to allow passage of fixation pins or bone screws, drills, taps, and awls through it in a predetermined trajectory. The guiding barrels may have more than one insertion location with variable or pre-determined trajectories offset from a single exit location. The guiding barrels of the single barrel embodiments of the drill guide may be movable by means of a pivoting mechanism to allow drilling holes into bone on both sides of the longitudinal axis of the bone plate. The guiding barrels of the double barrel embodiments of the drill guide assembly also preferably have a tab to engage a slot of the bone plate to prevent rotation of the drill guide assembly in relation to the bone plate. The single barrel embodiments of the drill guide assembly also preferably have a tab on the outer stem to engage a slot of the bone plate to prevent rotation of the drill guide assembly in relation to the bone plate.

The handle of the drill guide assembly may have a ratchet gear mechanism that permits incremental swiveling with respect to the axis of a button cam. The ratchet is operated by pressing and holding a button cam while turning the handle. The handle may lock at predetermined angle intervals.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
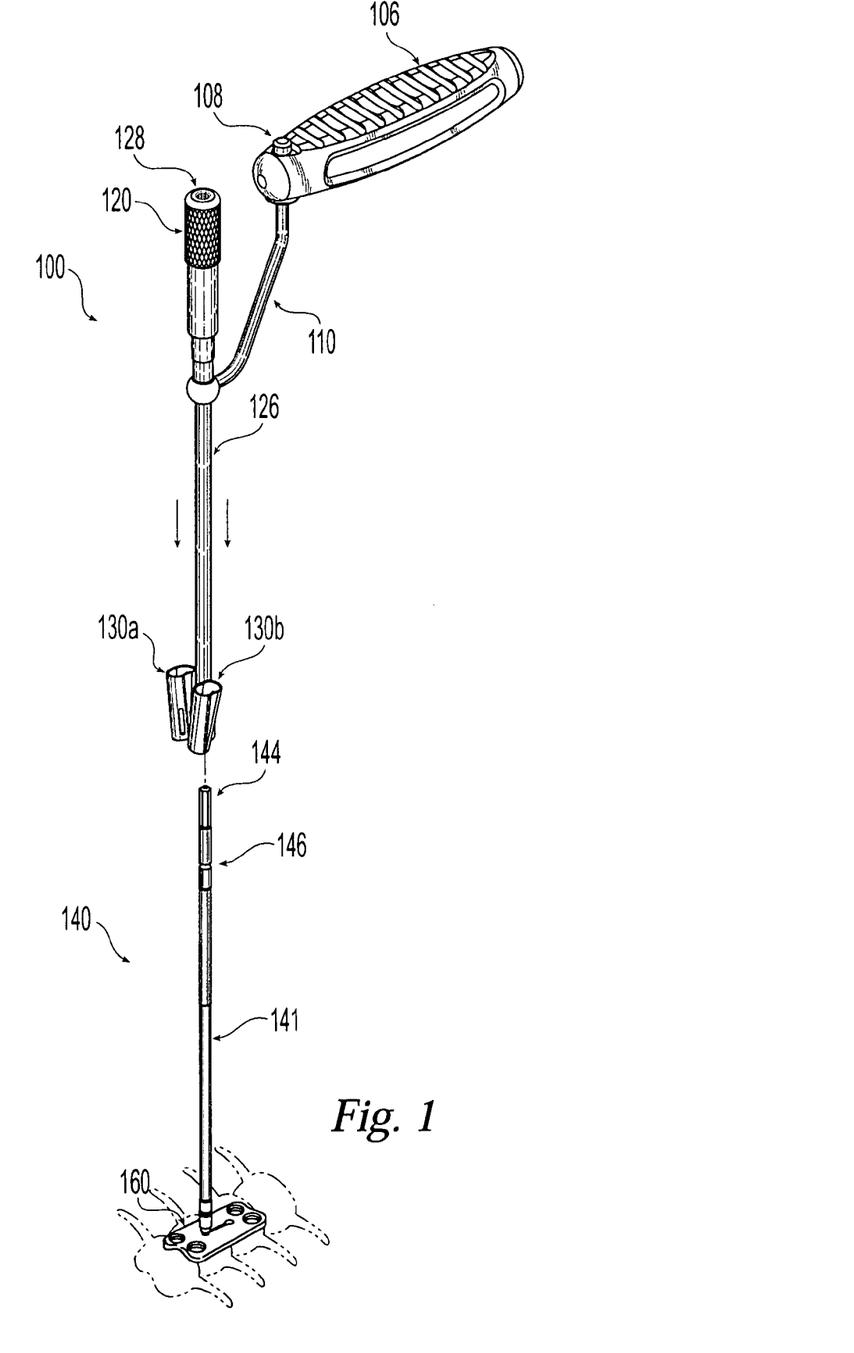
FIG. 1 is a perspective view of the double barrel drill guide assembly, the plate holder, and the bone plate.

Referring to FIG. 1, there is shown an exemplary double barrel drill guide assembly 100 and plate holder 140, which are adapted for use with a slotted cervical spine locking bone plate 160. While the bone plate, and plate holder and drill guide assembly are shown and described as a cervical plate for use in the cervical region of the spine, it will be appreciated that the bone plate features are applicable to other bone plates and that the drill guide assembly and plate holder are also usable with other bone plates. Assembly 100 includes a handle member 106, an offset handle stem 110, release sleeve 120, outer stem 126, and drill guiding barrels 130a and 130b. Handle member 106 of drill guide assembly 100 can be incrementally swiveled by pressing and holding button cam 108. Releasing the button cam 108 locks handle 106 in place with relation to offset handle stem 110.

Figure 2:
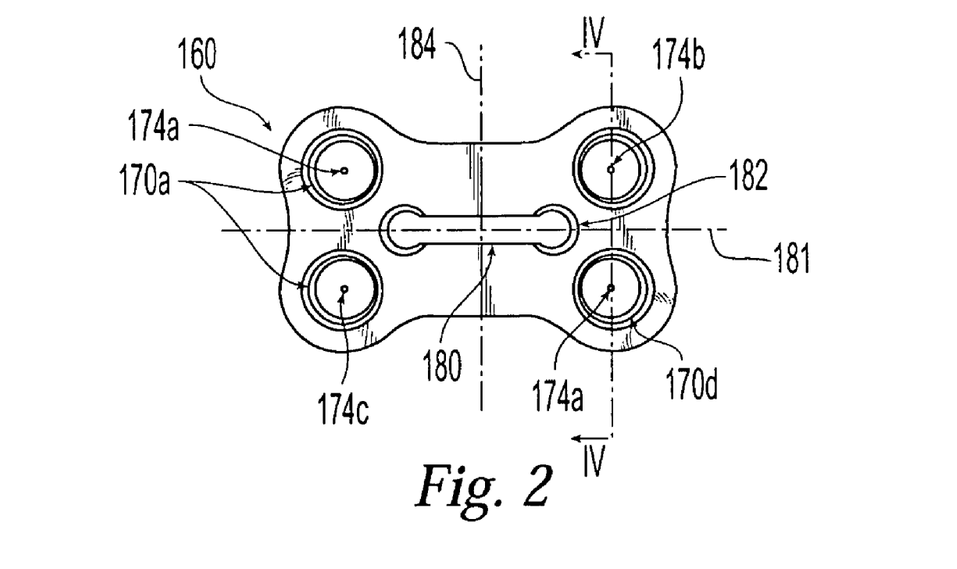
FIG. 2 is a top view of the bone plate of FIG. 1.
Figure 3:
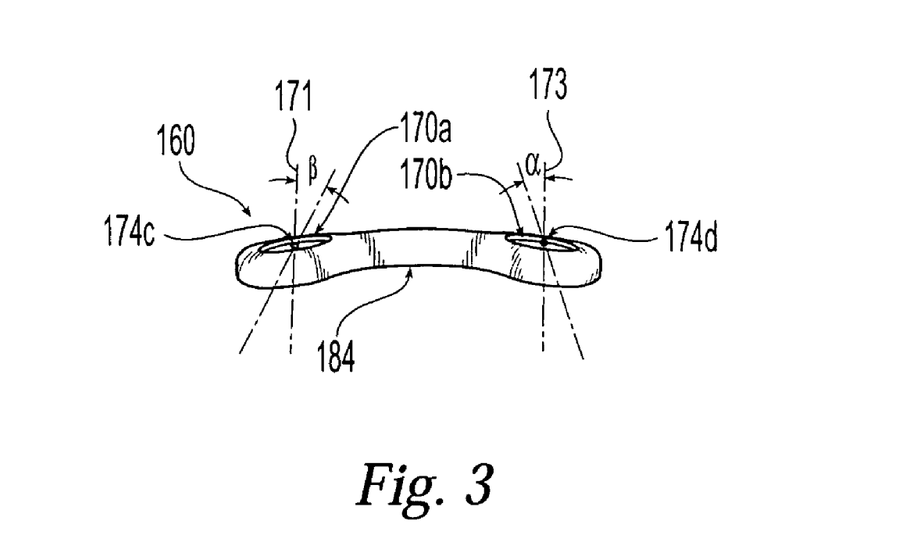
FIG. 3 is a side view of the bone plate of FIG. 1.
Figure 4:
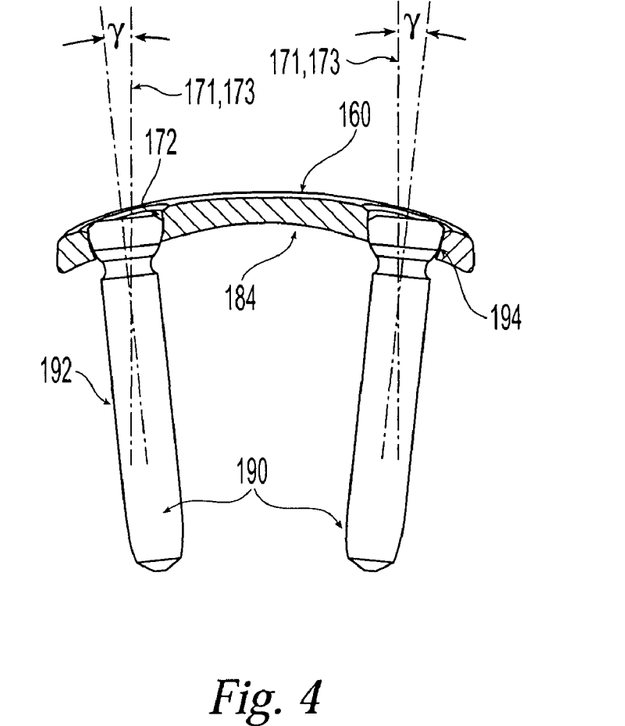
FIG. 4 is a cross-sectional view of the bone plate of FIG. 1 taken along line IV-IV in FIG. 2 with bone screws.

With reference to FIG. 2, cervical spine locking bone plate 160 is roughly dog-bone shaped with two pairs of fixation holes, upper fixation holes 170a, and lower fixation holes 170b; and a slot 180 along the longitudinal axis 181 of bone plate 160. Exemplary thicknesses of bone plate 160 range from approximately 1.5 mm to approximately 4 mm, although other thicknesses are possible and bone plate 160 can be fabricated from titanium, alloys of titanium, stainless steel, or other biocompatible materials. Each end of slot 180 preferably is threaded, countersunk, or both to allow plate holder 140 to be coupled to bone plate 160. As shown in FIGS. 3 and 4, underside 184 of bone plate 160 preferably is contoured along its longitudinal axis 181 and its transverse axis 184 to match the outer surface of the vertebrae to which it will be attached. Angles of fixation holes are determined in relation to axes 171, 173 perpendicular to a plane formed by points 174a-d (shown in FIGS. 2 and 3) centered over fixation holes 170a, 170b on the extended top surface of bone plate 160. In bone plates with more than two pairs of fixation holes, the end pairs of fixation holes are used to form the reference plane. The conical inner surfaces 172 of the fixation holes 170a, 170b are oriented so that the tips of bone fasteners bone screws 190 are locked at an inward angle $\gamma$ of about 1° to about 10°, preferably about 4.3°, with respect to axes 171, 173. FIG. 3 shows the upper pair of fixation holes 170a oriented so that the tips of bone fasteners 190 extend in an upward direction with respect to the spine at an angle $\alpha$ with respect to the axis 171. The lower pair of fixation holes 170b is oriented downward with respect to the spine at an angle $\beta$ with respect to axis 173. The upward angle $\alpha$ of the upper pair of fixation holes 170a can vary from 0 to 15°, and is preferably about 12°, while the downward angle $\beta$ of the lower fixation holes 170b can vary from 0 to 10°, and preferably is about 6°.

While the bone plate 160 has been shown as having two pairs of fixation holes 170a and 170b, the bone plate may have additional pairs of fixation holes 170c, 170d, etc., in order to bridge additional vertebrae. The fixation holes located between the fixation holes 170a, 170b located at the ends of the bone plate are preferably oriented perpendicular to the plane formed by the holes 170a, 170b, but may vary approximately 5° upward or downward with respect to the spine, and may angle toward the central longitudinal axis 181 as viewed from either end of bone plate 160 with an angle $\gamma$ that matches that of holes 170a, 170b. Additionally, while bone plate 160 has been illustrated and described with pairs of fixation holes, it may also be provided with a single fixation hole for each vertebra or combinations thereof.

Figure 7:
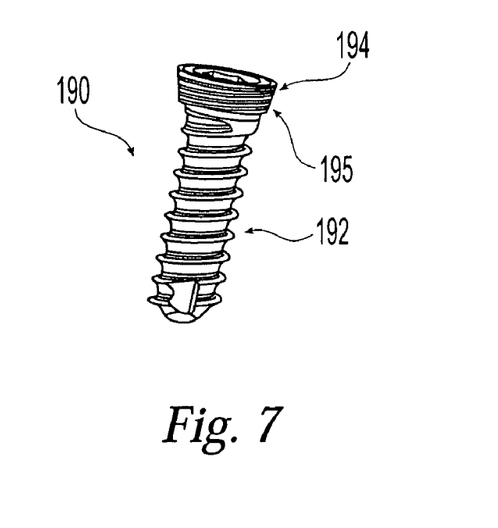
FIG. 7 is a perspective view of a bone screw to be used with the bone plates of FIGS. 2 through 6.

Fixation holes 170a, 170b may be threaded, with conical bone screw head 194 threaded to match, as shown in FIG. 7. Conical threads 195 of bone screw head 194 may have a higher pitch than the bone engaging lower threads 192. This difference in thread pitch between the conical threads 195 and the lower thread 192 results in compression between the plate and vertebra as the bone screw 190 is inserted.

Figure 5:
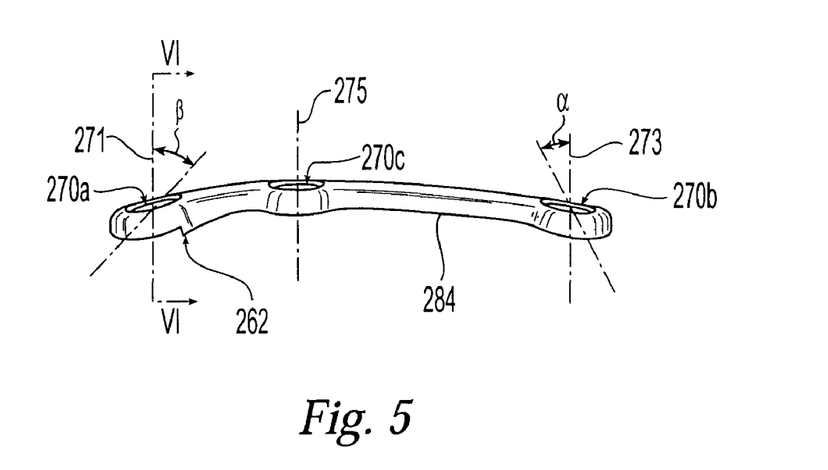
FIG. 5 is a side view of an alternative embodiment of the bone plate.
Figure 6:
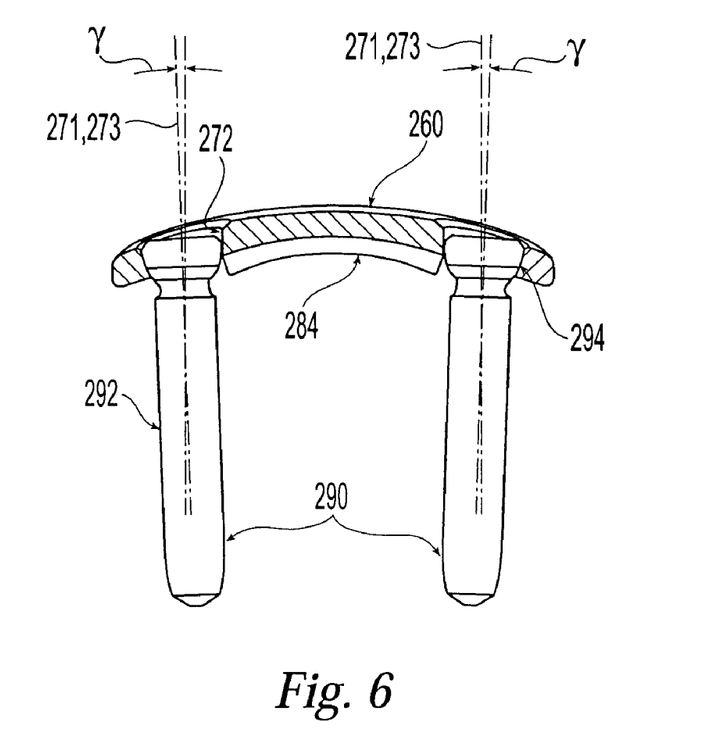
FIG. 6 is a cross-sectional view of the alternative embodiment of the bone plate of FIG. 5 taken along line VI-VI in FIG. 5 with bone screws.

FIG. 5 shows a side view of an alternative embodiment of the cervical spine locking bone plate. Bone plate 260 has three pairs of fixation holes 270a, 270b, 270c, although more than three pairs of fixation holes are possible. FIG. 6 is a cross sectional view of bone plate 260 with bone screws 190. As shown in FIGS. 5 and 6, underside 284 of bone plate 260 is contoured to match the outer surface of the vertebrae to which it will be attached. Angles $\alpha$, $\beta$ and $\gamma$ of holes 270a, 270b may take the same values as angles $\alpha$, $\beta$, and $\gamma$ of holes 170a, 170b of bone plate 160. Axes 275 of the additional pair of holes 270c are preferably perpendicular to the plane formed by the holes 270a, 270b, as viewed from the side of bone plate 260. As viewed from either end of bone plate 260, central axes 275 may have an orientation within the same range as angle $\gamma$ of axes 171, 173 of bone plate 160. FIGS. 5 and 6 also show an optional step feature 262, which preferably forms a shoulder or flange to accommodate the shape of the sacral promontory to facilitate placing bone plate 260 on the sacral plate. The step feature is also an optional feature of bone plate 160.

Figures 8, 8A, 8B:
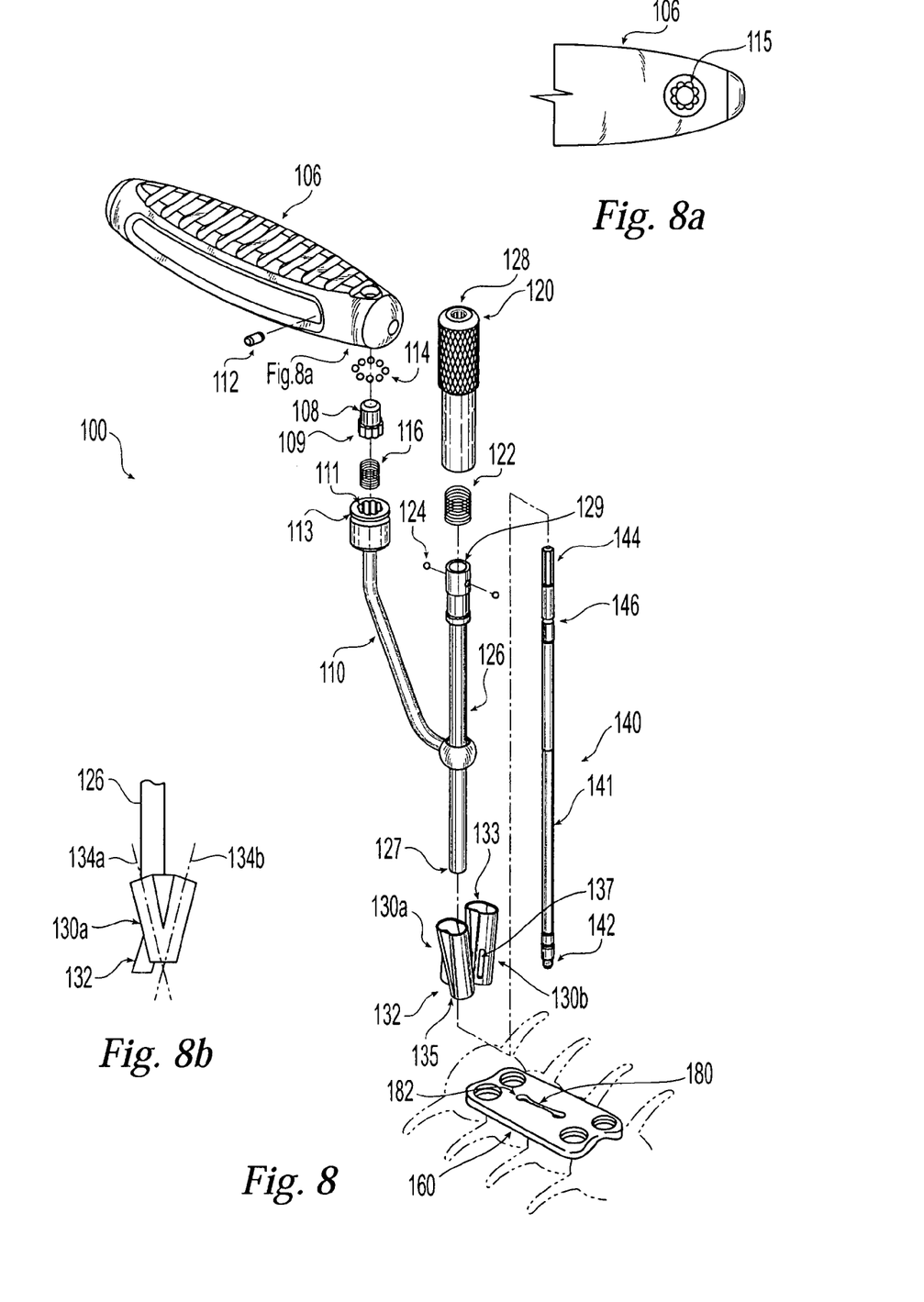
FIG. 8 is a perspective exploded view of the double barrel drill guide assembly of FIG. 1.
FIG. 8a is a detail of the underside of the handle member of the double barrel drill guide assembly shown in FIG. 8.
FIG. 8b is a detail view of a drill guiding barrel with two insertion locations forming passageways along two axes.

Referring to FIG. 8, plate holder 140 includes rod 141 that preferably is cylindrical for most of its length (preferably approximately 200 mm long), preferably with threads 143 at distal end 142 of rod 141. Rod 141 couples to bone plate 160. Bone plate 160 preferably has threads 183 at end 182 of slot 180 to mate with threads 143 at distal end 142 of rod 141. Alternatively, distal end 142 of plate holder 140 may have expandable bushings that mate with a counterbored end 182 of slot 180 of bone plate 160. Proximal end 144 of plate holder 140 may have a non-circular cross-section, such as a hexagonal shape. Non-circular shapes other than hexagonal may also be used. Below proximal end 144 of plate holder 140 is a radial groove 146. Plate holder 140 allows a user to manipulate bone plate 160, 260 from a remote position without touching the plate.

As shown in FIG. 8, drill guide assembly 100 is coupled to plate holder 140 by sliding distal end 127 of outer stem 126 of drill guide assembly 100 over proximal end 144 of rod 141. Release sleeve 120 is connected to proximal end 129 of outer stem 126 in a captive non-releasable manner, such as for example, by swaging. Release sleeve 120 can be moved axially within a limited range and can be rotated with respect to outer stem 126. Spring 122 is held captive inside release sleeve 120 above proximal end 129 of outer stem 126, biasing release sleeve 120 away from proximal end 129 of outer stem 126. Ball detents 124 normally protrude into the bore of outer stem 126, preventing sliding outer stem 126 over plate holder 140. Release sleeve 120 is pressed axially toward distal end 127 of outer stem 126 against the bias of release spring sleeve 122 to permit ball detents 124 to move outward into an area of greater inside diameter (not shown) of the release sleeve 120, allowing drill guide assembly 100 to be pushed farther onto plate holder 140. Removing pressure from release sleeve 120 results in the bias of release sleeve spring 122 returning release sleeve 120 to its axial position farthest from bone plate 160, forcing ball detents 124 inward to engage radial groove 146 in plate holder 140, locking drill guide assembly 100 to plate holder 140.

Release sleeve 120 has a non-circular, preferably hexagonal, hole 128 at its upper end, the perimeter of which hole 128 engages non-circular proximal end 144 of plate holder 140. Although hole 128 and proximal end 144 are shown as hexagonal, it will be appreciated that other mating shapes are possible. Release sleeve 120 can be rotated in relation to outer stem 126 to screw and unscrew plate holder 140 to allow engagement of plate holder 140 with, and disengagement of plate holder 140 from, bone plate 160. Although the connection between the drill guide assembly and the plate holder has been described as a stem coaxial with and sliding over a rod, other embodiments are possible including, for example, a drill guide assembly with a stem attaching to the side of a plate holder.

Handle member 106 is offset from outer stem 126 by offset handle stem 110, allowing greater visibility and access to bone plate 160 and vertebrae. Handle stem 110 is mechanically attached to outer stem 126, for example by welding, brazing, or friction fit. Handle member 106 can be pivoted about offset handle stem 110 by pressing button cam 108 and rotating handle member 106, providing still greater visibility and access as the surgeon alternates sides of plate 160 and vertebrae on which he is working. Handle member 106 is retained on handle stem 110 by means of a set screw 112 loosely engaging a handle stem radial groove 113. Pressing button cam 108 against the bias of cam spring 116 moves the detents 109 of the button cam 108 out of engagement with detent grooves 115 (shown in FIG. 8a) in handle member 106 while the detents 109 remain engaged with detent grooves 111 of handle stem 110, allowing handle member 106 to be rotated with respect to offset handle stem 110, with optional ball bearings 114 facilitating rotation. Releasing pressure on button cam 108 allows cam spring 116 to return detents 109 of button cam 108 to engagement with detent grooves 115 of handle member 106, while maintaining engagement between detents 109 of button cam 108 and detent grooves 111 of handle stem 110, preventing rotation of handle member 106 in relation to handle stem 110.

Drill guiding barrels 130a, 130b are mechanically attached to outer stem 126, for example by brazing, welding, or friction fit. Drill guiding barrels 130a, 130b may have multiple insertion locations 133 with predetermined trajectories forming passageways that are aligned through a single exit location 135. For example, FIG. 8b shows drill guiding barrel 130a with two insertion locations 133 forming passageways along axes 134a, 134b. One trajectory may be substantially perpendicular to the bone plate while other trajectories may be offset and/or inclined with respect to the perpendicular trajectory. The predetermined trajectories preferably match the various trajectories of fixation holes 170 of bone plate 160 and allow greater precision than is possible with adjustable trajectory drill guides. The drill guiding barrels are shown with two insertion locations 133 and two predetermined trajectories. However, there may be additional insertion locations 133 with other predetermined trajectories to allow the drill guide to be used with a variety of bone plates. Optionally, drill guiding barrels 130a, 130b may have a single insert location 133 and a single exit location 135. Finally, drill guiding barrels 130a, 130b may have a single insertion location 133 and more than one exit location 135, or multiple insertion locations 133 and multiple exit locations 135. Guiding barrels 130a, 130b are preferably sized to allow passage of fixation pins or bone screws, drills, taps, and awls. Slotted holes 137 in guiding barrels 130a, 130b allow a surgeon to see the fixation components and tools as they are inserted into the guiding barrels 130a, 130b. Drill guiding barrels 130a and 130b have a tab 132 that engages slot 180 of bone plate 160 to prevent rotation of drill guide assembly 100 in relation to bone plate 160.

Figures 9, 9A, 9B:
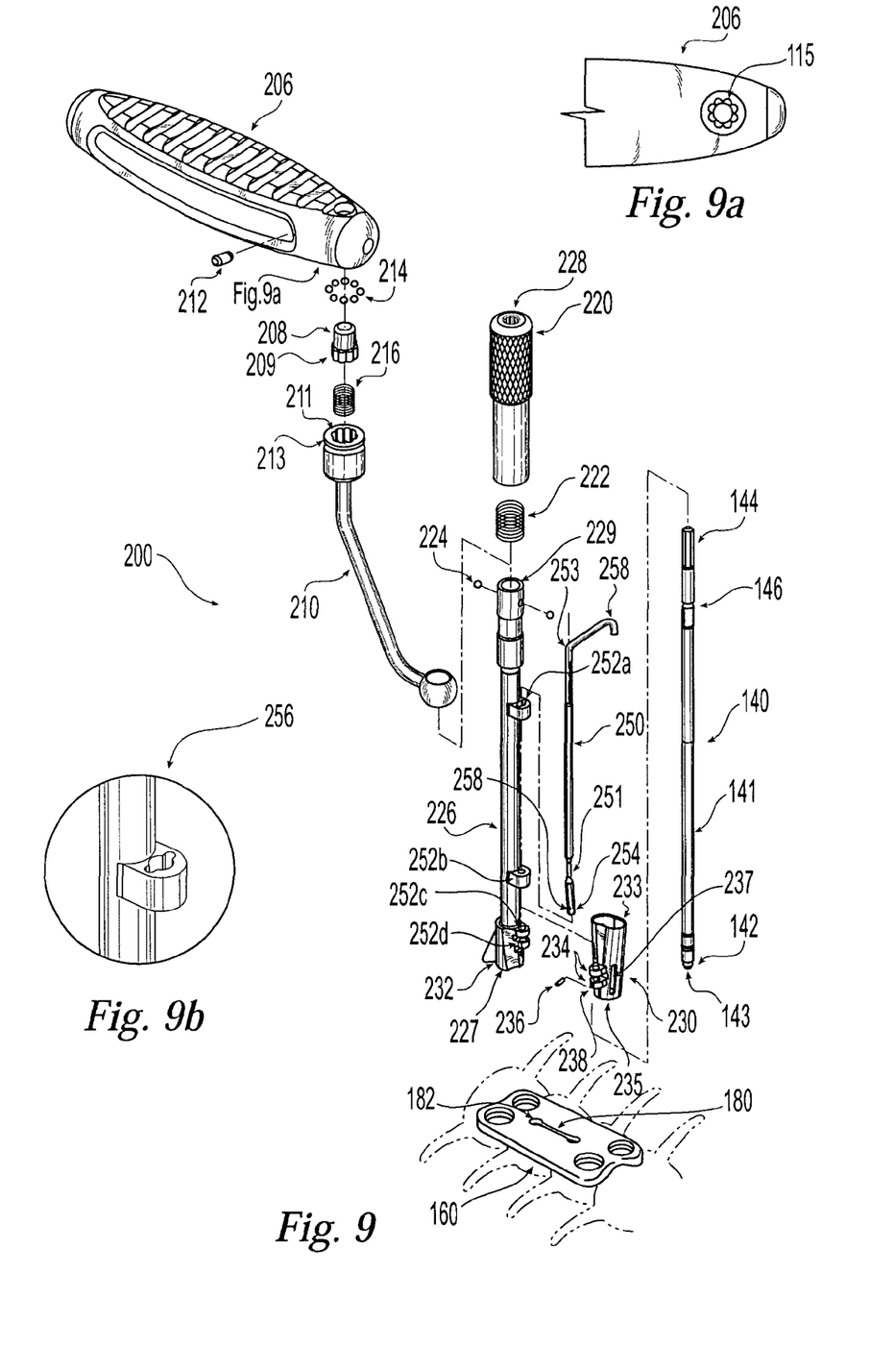
FIG. 9 is a perspective exploded view of the single barrel drill guide assembly.
FIG. 9a is a detail of the underside of the handle member of the single barrel drill guide assembly shown in FIG. 9.
FIG. 9b is a detail of the flex shaft receiving groove of the single barrel drill guide assembly shown in FIG. 9.

FIG. 9 shows an exploded view of an exemplary single barrel drill guide assembly 200 and plate holder 140, which are adapted for use with slotted cervical spine locking bone plate 160. While the bone plate, and plate holder and drill guide assembly are shown and described as a cervical plate for use in the cervical region of the spine, it will be appreciated that the drill guide assembly and plate holder are also usable with other bone plates. Assembly 200 includes a handle member 206, an offset handle stem 210, release sleeve 220, outer stem 226, and drill guiding barrel 230. Handle member 206 of drill guide assembly 200 can be incrementally swiveled by pressing and holding button cam 208. Releasing button cam 208 locks the handle in place with relation to the handle stem 210.

Figure 10:
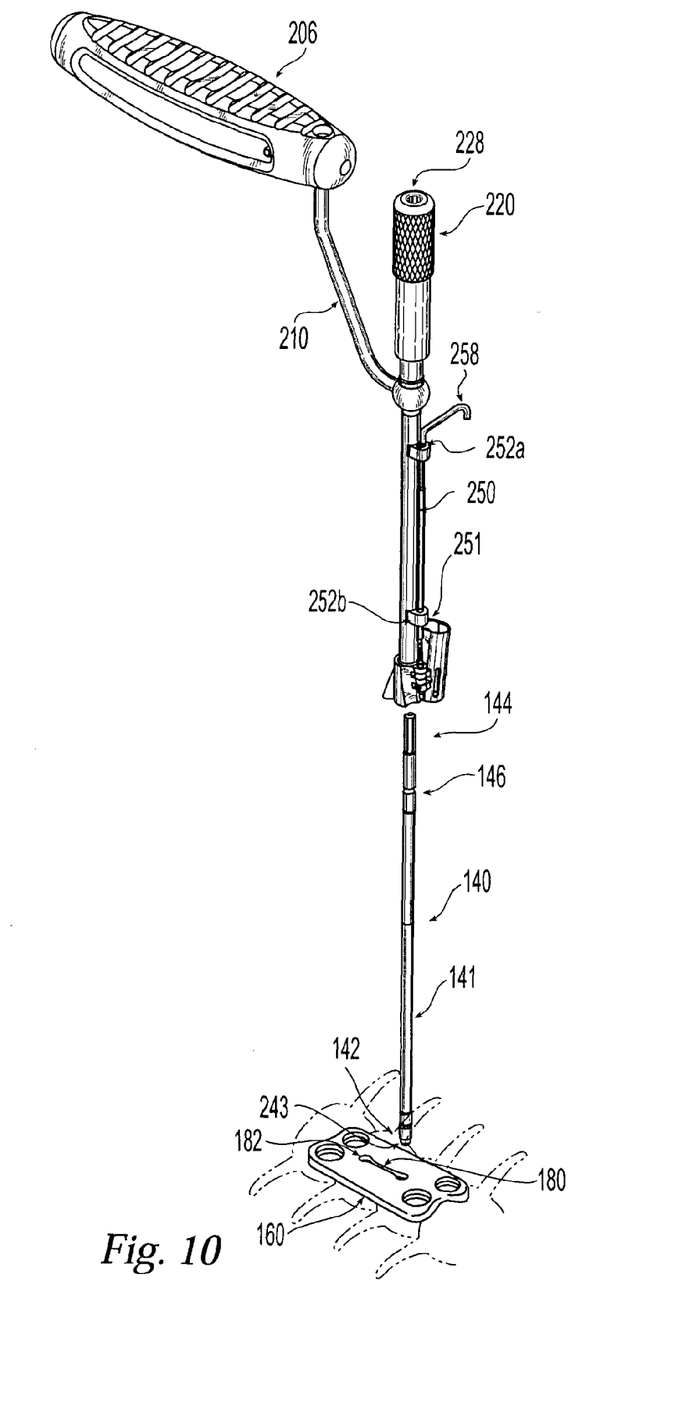
FIG. 10 is a perspective view of the single barrel drill guide assembly.

As shown in FIGS. 9 and 10, drill guide assembly 200 is coupled to plate holder 140 by sliding distal end 227 of outer stem 226 of the drill guide assembly 200 over proximal end 144 of plate holder 140. Ball detents 224 normally protrude into the bore of outer stem 226, preventing sliding outer stem 226 over plate holder 140. Release sleeve 220 is pressed axially toward distal end 227 of outer stem 226 against the bias of release spring sleeve 222 to permit ball detents 224 to move outward into an area of greater inside diameter (not shown) of the release sleeve 220, allowing drill guide assembly 200 to be pushed farther onto plate holder 140. Removing pressure from release sleeve 220 results in the bias of release sleeve spring 222 returning release sleeve 220 to its axial position farthest from bone plate 160, forcing ball detents 224 inward to engage plate holder radial groove 146, locking drill guide assembly 200 to plate holder 140. Outer stem 226 has a locking tab 232 at its distal end that is inserted into slot 180 of locking plate 160 to prevent rotation of, and provide alignment of, the drill guide assembly 200 in relation to the bone plate 160.

Release sleeve 220 has a hexagonal hole 228 at its upper end, the perimeter of which hole 228 engages hexagonal proximal end 244 of plate holder 240. Although hole 228 and proximal end 144 are shown as hexagonal, it will be appreciated that other mating shapes are possible. Release sleeve 220 can be rotated with respect to outer stem 226 to screw plate holder 140 into, and unscrew plate holder 140 from, the bone plate 160.

Handle member 206 is offset from outer stem 226 by offset handle stem 210, allowing greater visibility and access to the bone plate and vertebrae. Handle member 206 can be pivoted about handle stem 210 by pressing button cam 208 and rotating handle member 206, providing still greater visibility and access as the surgeon alternates sides of the bone plate 160 and vertebrae on which he is working. Handle member 206 is retained on handle stem 210 by means of a set screw 212 loosely engaging handle stem radial groove 213. Pressing button cam 208 against the bias of cam spring 216 moves detents 209 of button cam 208 out of engagement with detent grooves 215 (shown in FIG. 9a) in handle member 206 while detents 209 remain engaged with detent grooves 211 of handle stem 210, allowing handle member 206 to be rotated in relation to handle stem 210. Releasing pressure on button cam 208 allows cam spring 216 to return detents 209 of button cam 208 to engagement with detent grooves 215 of handle member 206, while maintaining engagement between detents 209 of button cam 208 and detent grooves 211 of handle stem 210, preventing rotation of handle member 206 in relation to handle stem 210.

Single barrel drill guide assembly 200 offers the advantage of greater visibility for the surgeon because only one side of the plate is obscured by drill guiding barrel 230 at a time. Drill guiding barrel 230 is attached to outer stem 226 by flex shaft 250 (approximately 90 mm long in its major dimension and approximately 2 mm in diameter) made of stainless steel or other flexible biocompatible material, which passes through stem hinge projections 252a-d on outer stem 226 and drill guiding barrel hinge projections 234 on drill guiding barrel 230. Flex shaft 250 is bent to provide a finger lever 258 for manipulating the drill guiding barrel 230. Dowel pin 236 is inserted through drill guiding barrel dowel pin hole 238 in drill guiding barrel hinge projection 234 and flex shaft dowel pin hole 254 in flex shaft 250 to lock the drill guiding barrel 230 to flex shaft 250 so that the drill guiding barrel 230 and flex shaft 250 rotate together within stem hinge projections 252a-d. Flex shaft 250 has a reduced diameter section 251, for example approximately 1 mm for a length of 9 mm. Lower stem hinge projections 252c, 252d are offset from upper stem hinge projections 252a, 252b, causing flex shaft 250 to be slightly bowed at reduced diameter section 251, creating a spring force biasing flex shaft finger lever 258 in the direction of. Upper stem hinge projection 252a has flex shaft receiving grooves 256a, 256b that receive the inner radius 253 at the location where flex shaft 250 bends to form flex shaft finger lever 258, locking drill guiding barrel 230 on either left or right side, respectively, of drill guide assembly 200. Drill guiding barrel 230 is moved from left to right side by pulling flex shaft 250 upward until the flex shaft finger lever 258 is clear of flex shaft receiving groove 256a and rotating combined locking drill guide barrel 230 and flex shaft 250 until flex shaft finger lever 258 is positioned above flex shaft receiving groove 256b. Releasing flex shaft 250 allows flex shaft finger lever 258 to seat in flex shaft receiving groove 256b due to the spring force of bowed flex shaft lower end 259, the spring force resulting from the bow in reduced diameter section 251 of flex shaft 250.

Preferably, drill guiding barrel 230 has multiple insertion locations 233 with predetermined trajectories preferably inclined or offset from a single exit location 235, although a drill guiding barrel 230 with a single insertion location 233 and a single exit location 235 is possible. In addition, a drill guiding barrel 230 with a single insertion location 233 and more than one exit location 235 is possible. Multiple insertion locations 233 provide proper trajectories when drill guiding barrel 230 is moved to alternate sides of the plate and also provide for the various trajectories needed for the upper and lower fixation holes 170a, 170b of bone plate 160. The predetermined trajectories allow greater precision than possible with adjustable trajectory drill guides. Guiding barrel 230 allows passage of fixation pins or bone screws, drills, taps, and awls. Slotted holes 237 in guiding barrel 230 allow a surgeon to see the fixation components and tools as they are inserted into the guiding barrel 230.

Figures 11, 12:
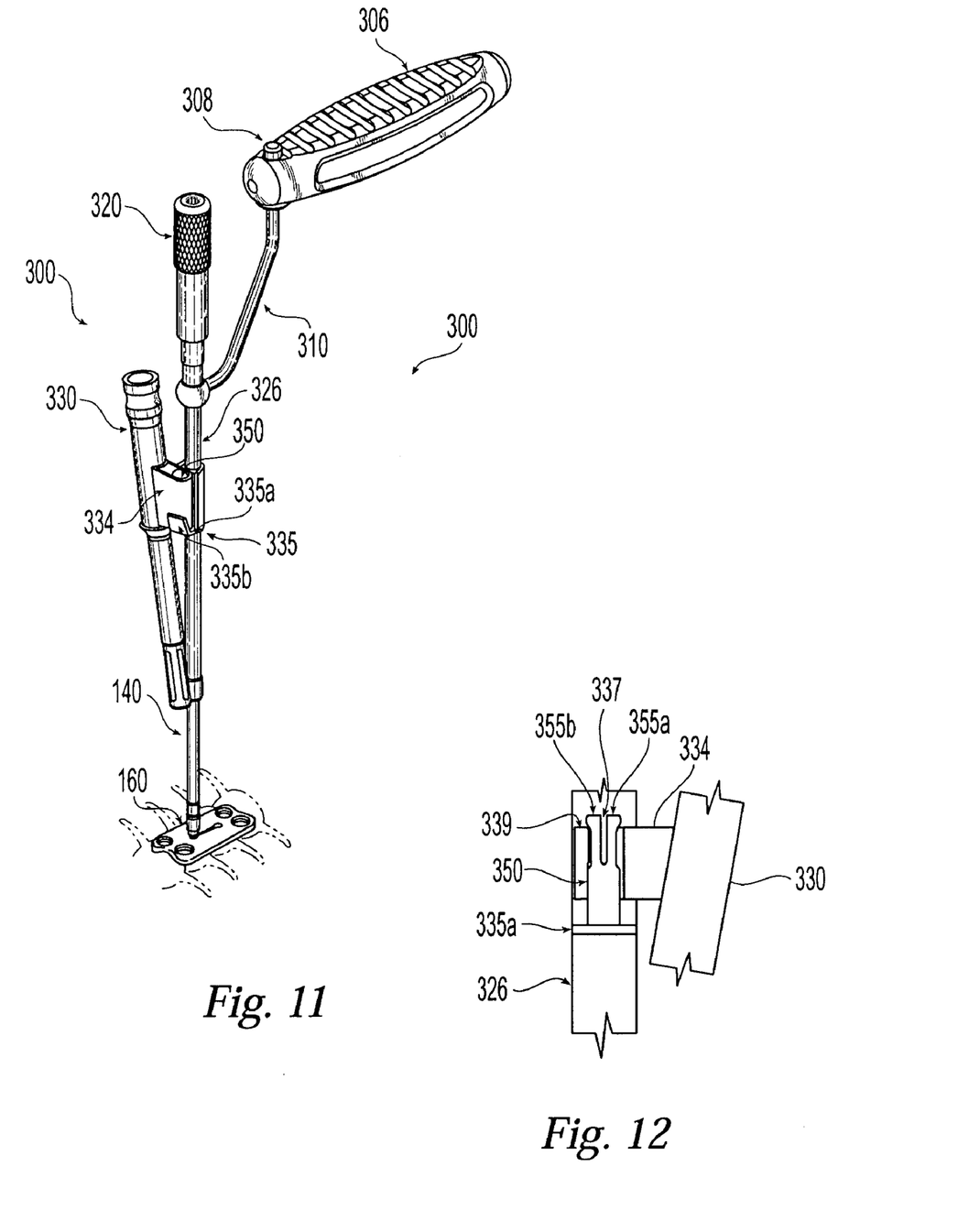
FIG. 11 is a perspective view of an alternative embodiment of the single barrel drill guide assembly.
FIG. 12 is a detail of the hinge connection between the drill guiding barrel and the outer stem of the alternative embodiment of the single barrel drill guide assembly shown in FIG. 11.

FIG. 11 shows an alternate embodiment of a single barrel drill guide. Drill guide assembly 300 has a relatively long (representative length: approximately 80 mm) drill guiding barrel 330 with a depth stop (a shoulder, not shown) inside the drill guiding barrel 330 (representative outside diameter: approximately 10-12 mm) that stops the drill bit at a predetermined depth. Handle member 306, button cam 308, offset handle stem 310, outer stem 326, and release sleeve 320 correspond to handle stem 106, button cam 108, offset handle stem 110, outer stem 126, and release sleeve 120 of drill guide assembly 100. Tab 335 is attached to outer stem 326, preferably by welding or brazing, and has a horizontal section 335a and vertical section 335b. Pin 350 is attached to tab horizontal section 335a, preferably by welding, brazing, or mechanical connection; and is parallel to outer stem 326. Pin 350 has a slot 337 beginning at its upper end and extending through a portion of the length of pin 350. Slot 337 separates hemispherical retainers 355a, 355b, which have a greater diameter than the section of pin 350 below the retainers 355a, 355b. Retainers 355a, 355b secure drill guiding barrel hinge 334 on pin 350. To switch drill guiding barrel 330 to the opposite side of bone plate 160, the surgeon pulls drill guiding barrel 330 towards himself so that drill guiding barrel hinge 334 clears tab vertical section 335b, allowing the surgeon to pivot the drill guiding barrel 330 to the opposite side. The surgeon's pulling of drill guiding barrel 330 toward himself forces the retainers 355a, 355b closer together as upper surface 339 of drill guiding barrel hinge 334 contacts retainers 355a, 355b, creating a spring force biasing drill guide barrel hinge 334 away from the surgeon. The drill guiding barrel 330 is then released and returned to its lower position by the spring force of the compressed retainers 355a, 355b against upper surface 339 of drill guide barrel hinge 334 such that drill guiding barrel hinge 334 is held in angular position by tab 335.

The method of drilling holes in vertebrae with the system disclosed above is now described. A surgeon inserts a plate holder into a slotted hole in a bone plate. The surgeon then releasably locks a drill guide assembly onto the plate holder. The bone plate is applied to the appropriate vertebrae by a surgeon holding a handle of the drill guide assembly. The surgeon then aligns a drill bit with the appropriate insertion location in the appropriate drill guiding barrel of the drill guide assembly and inserts the drill bit into the drill guiding barrel. The surgeon then drills a first hole coaxial with the central axis of a first fastener hole in the plate. A first bone screw is then inserted into the drill guiding barrel and threaded into the first hole. If a double barrel drill guide assembly is being used, the surgeon then aligns the drill bit with the appropriate insertion location of the adjacent drill guiding barrel. If a single barrel drill guide assembly is being used, the surgeon pivots the drill guiding barrel until it is aligned above a fastener hole adjacent to the first fastener hole in the plate and aligns the drill bit with the appropriate insertion location of the drill guiding barrel. The surgeon then drills a second hole coaxial with the central axis of a second fastener hole in the plate and installs a second bone screw. The surgeon then rotates counterclockwise a release sleeve on the drill guide assembly, which disengages the plate holder from the plate. The surgeon removes the drill guide assembly and attached plate holder from the plate and inserts the plate holder into a second hole in the bone plate by rotating the release sleeve counterclockwise, the process of drilling holes and installing bone screws in adjacent through holes of the plate and removing the drill guide assembly and plate holder is repeated until all pairs of adjacent holes have been drilled and bone screws inserted.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. For example, various means may be used to attach the plate holder to the bone plate or to the drill guide assembly. In addition, the plate may be of various thicknesses, shapes, and contours; and have various fixation hole configurations.

What is claimed is:

1. A surgical drill guide assembly comprising:
   an outer stem having a bore and a longitudinal axis;
   at least one drill guiding barrel having a passageway, the passageway having a predetermined trajectory, the predetermined trajectory being at a substantially fixed angle with respect to the outer stem, the at least one drill guiding barrel being attached to the outer stem and configured to receive and guide a surgical drill bit, wherein the at least one drill guiding barrel is movably attached to the outer stem such that the fixed angle of the drill guiding barrel remains constant throughout movement of the drill guiding barrel about the outer stem;
   a rod at least partially disposed in the bore and releasably attached to both the outer stem and a bone plate; and
   a release mechanism for securing the outer stem to the rod, wherein the drill guide barrel pivots about a hinge on the stem.

2. The surgical drill guide assembly of claim 1, further comprising a tab attached to outer stem, wherein the tab has a horizontal section and a vertical section.

3. The surgical drill guide assembly of claim 2, wherein the tab includes a pin for receiving the drill guide barrel so that the drill guide barrel is axially moveable with respect to the pin and pivotable about the pin.

4. The surgical drill guide assembly of claim 3, wherein the at least a portion of the drill guide barrel is sized and configured to be seated on the horizontal section of the tab and wherein the drill guide barrel is pivotable by axially moving the drill guide barrel with respect to the tab so that the drill guide barrel clears the vertical section of the tab.

5. A surgical drill guide assembly comprising:
   an outer stem having a first longitudinal axis;
   a drill guiding barrel configured to receive and guide a surgical drill bit, the drill guiding barrel being pivotably attached to the outer stem, the drill guiding barrel being pivotable about an axis of rotation disposed outside of the outer stem and substantially parallel to the first longitudinal axis; and
   a rod releasably secured to the outer stem.

6. The surgical drill guide assembly of claim 5, wherein the drill guiding barrel has a depth stop for preventing a drill bit from exceeding a pre-determined depth.

7. The surgical drill guide assembly of claim 5, wherein the drill guiding barrel is attached to the outer stem by a hinge.

* * * * *